United States Patent [19]

Boux et al.

[11] 4,092,538
[45] May 30, 1978

[54] DEVICE FOR CHECKING THE IRRADIATION DOSE MEASURING CIRCUITS USED TO MEASURE THE IRRADIATION DOSES DELIVERED BY A RADIOTHERAPY APPARATUS

[75] Inventors: René Boux; Claude Levaillant, both of Paris, France

[73] Assignee: C.G.R. MeV, Paris, France

[21] Appl. No.: 696,900

[22] Filed: Jun. 17, 1976

[30] Foreign Application Priority Data

Jun. 20, 1975 France .................................. 75 19412

[51] Int. Cl.² ............................ G01T 1/17; H05G 1/26
[52] U.S. Cl. ...................................... 250/336; 250/401; 250/413
[58] Field of Search ................ 250/336, 374, 401, 413

[56] References Cited

U.S. PATENT DOCUMENTS

| 3,486,025 | 12/1969 | Brinkerhoff et al. | 250/336 X |
| 3,911,273 | 10/1975 | Franke | 250/401 X |
| 3,953,736 | 4/1976 | Kubisiak et al. | 250/336 X |
| 3,974,385 | 10/1976 | Grim | 250/413 X |
| 3,988,587 | 10/1976 | Shreve et al. | 250/336 X |

Primary Examiner—Archie R. Borchelt
Attorney, Agent, or Firm—Oblon, Fisher, Spivak, McClelland & Maier

[57] ABSTRACT

Device making it possible to check, prior to or after each irradiation treatment session, the proper operation of the dose-measuring systems associated with a radiotherapy apparatus and comprising at least one dose-measuring circuit equipped with a counter system of preselect design. This device comprises a pulse generator G, means for applying said pulses to the counter system of at least one of the measuring circuits and means making it possible to halt the generator G and reset the counter system to zero when coincidence occurs between the preselected number of pulses corresponding to a preselected dose level D and the displayed number of pulses corresponding to the dose level effectively delivered by an irradiation source S.

7 Claims, 4 Drawing Figures

DEVICE FOR CHECKING THE IRRADIATION DOSE MEASURING CIRCUITS USED TO MEASURE THE IRRADIATION DOSES DELIVERED BY A RADIOTHERAPY APPARATUS

Radiation beam generators and more particularly radiotherapy apparatus, are generally associated with a system which makes it possible to measure the radiation dose they are producing and with means for automatically stopping the radiation source when the delivered dose reaches a predetermined value.

In order to increase safety of operation of radiotherapy apparatus, some of them are equipped with a double dose-measuring circuit, the second measuring cirucit being arranged to stop operation of the radiation source when the irradiation dose is reached and in the event that the first measuring circuit, due to a defect, has not triggered the cut-off device.

However, there is no method of checking the operation of the measuring circuits prior to a treatment session.

The monitoring device in accordance with the invention makes it possible to perform such a check.

In accordance with the invention, a device for checking the operation of an irradiation dose-measuring system, said dose-measuring system being equipped with a first measuring circuit and a second measuring circuit, so-called "stand-by" measuring circuit, each incorporating a counter system designed to measure the irradiation does and to control halting of an radiation source S when the indicated dose level corresponds to a preselected dose level, said checking device comprising a pulse generator, first means for applying said pulses to said counter system of at least one of said measuring circuits, and second means which make it possible to halt the pulse generator and reset the counter systems to zero when coincidence is achieved between the preselected number of pulses corresponding to said preselected dose level D and the counted number of pulses and means for controlling the halting of operation of the irradiation source S.

For a better understanding of the invention and to show how the same may be carried into effect, reference will be made to the drawings, given solely by way of example, which accompany the following description, and wherein.

A system for measuring irradiation dose level can be provided with two dose-measuring circuits, one of them, known as the "main circuit", being designed to control the halting of the irradiation source when the indicated dose level corresponds with the preselected dose level D, and the other, known as the "secondary circuit" or "stand-by circuit", being designed to control the halting of the irradiation source when the main circuit is defective. Means are then associated with the second measuring circuit, which make it possible to introduce a delay into the measuring of the dose in relation to the dose-measuring function performed by the main circuit.

The checking device in accordance with the invention makes it possible to check proper operation of these dose-measuring circuits.

In a first embodiment (FIG. 2), the checking device in accordance with the invention makes it possible to check the dose-measuring circuits A and/or B prior to each radiotherapy proper operating of a first and a second treatment session.

In a second embodiment (FIG. 4), the checking device in accordance with the invention makes it possible to check the measuring circuits at the end of each treatment session or, more precisely to check the second dose measuring circuit after the first dose-measuring circuit has recorded coincidence between the indicated dose level and the preselected dose level D, and has initiated the halting of the irradiation sources.

Figure 1:
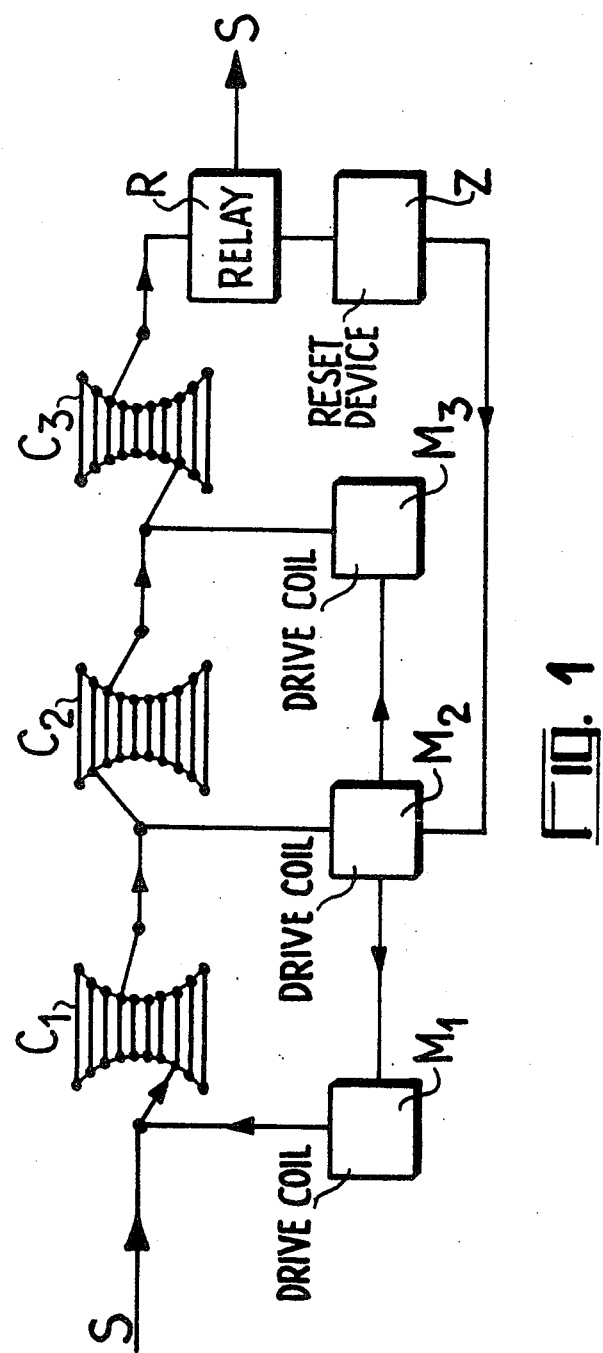
FIG. 1 illustrates a conventional electromechanical counter of the kind used in a monitoring device in accordance with the invention.

These two dose-measuring circuits each comprise, in the described examples, three electromechanical counters $C_1$, $C_2$, $C_3$ of known kind, producing a preselected display (FIG. 1). When the set of three counters $C_1$, $C_2$, $C_3$ of the main circuit, these respectively indicating the units digit, the tens digit and the hundreds digit, registers a number corresponding to the preselected number, a circuit controlling a safety relay R authorises this relay R to halt the operation of the source S producing the irradiation beam, and to trigger the system Z which resets the counters $C_1$, $C_2$, $C_3$.

Figure 2:
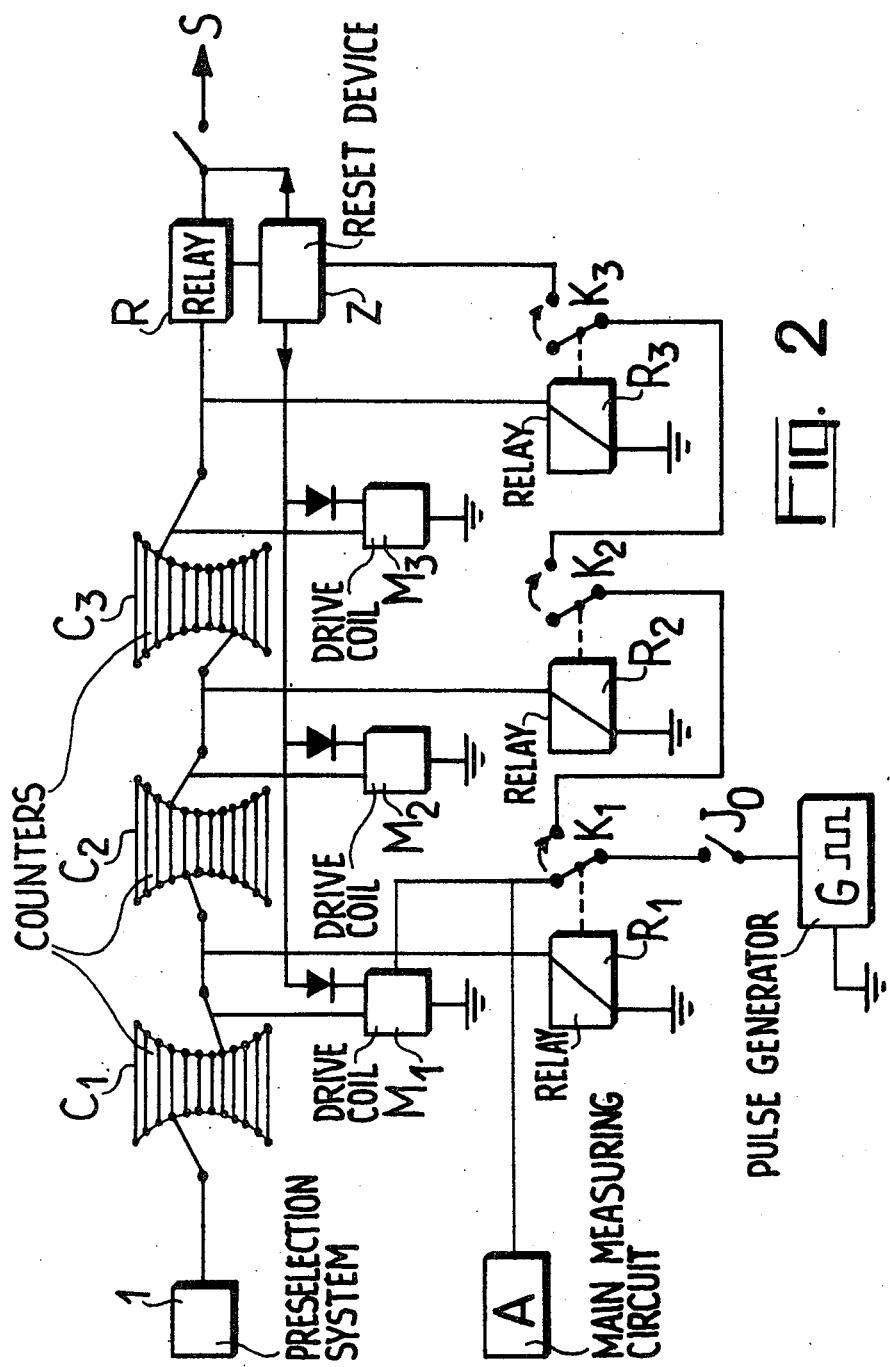
FIGS. 2, 3 and 4 illustrate three embodiments of a monitoring device in accordance with the invention.

In the first embodiment, the checking device in accordance with the invention, which makes it possible to check the measuring circuits A and B, has been shown schematically in FIG. 2. It comprises means making it possible to apply fast pulses to the counter system in order to be able to check, prior to each treatment session by means of an irradiation source S, that the measuring (or measuring circuits) is (or are) operating properly. (Only the measuring circuit A and its associated checking device are shown in FIG. 2).

This checking device comprises a pulse generator G, a contactbreaker $J_O$, a first relay $R_1$ and a first drive coil $M_1$ associated with the counter $C_1$ responsible for the unit digits for example, a reversing switch $K_1$, a second relay $R_2$ and a second drive coil $M_2$ associated with the counter $C_2$, a reversing switch $K_2$, a third relay $R_3$ and a third drive coil $M_3$ associated with a counter $C_3$ (these counters $C_1$, $C_2$, $C_3$ corresponding respectively to the units, tens and hundreds digits), the safety relay R being provided for controlling the halting of the operation of the irradiation source S. A light or audio signal can likewise be triggered by the safety relay R.

Before irradiation, when the checking device is operating, the pulses furnished by the pulse generator G are applied to the coil $M_1$ by means of the relay $R_1$, causing the first counter $C_1$ to advance until it indicates the preselected digit. The relay circuit then closes, the supply is disconnected from the coil $M_1$ and the counter $C_1$ stops. The reversing switch $K_1$ changes state and the pulses are supplied to the counter $C_2$ by means of the drive coil $M_2$. Upon coincidence between the displayed digit and the preselected digit, the relay $R_2$ closes, the reversing switch $K_2$ changes state and the pulses are supplied to the counter $C_3$ by means of the drive coil $M_3$. When the digit displayed by the counter $C_3$ coincides with the preselected digit, the relay $R_3$ controls the automatic halting of the pulse generator and operates the reset system Z for the counters $C_1$, $C_2$, $C_3$, thus allowing the setting into operation of the irradiation source S.

The checking device as illustrated in FIG. 2 is associated with the electromechanical counters $C_1$, $C_2$, $C_3$ of a dose-measuring circuit A. When the dose-measuring system comprises two measuring circuits A and B, the checking device as described and illustrated in FIG. 2 can be used to successively check both measuring circuits, a reversing switch making it possible to supply pulses from the generator G successively to the two measuring circuits. It is also possible to associate a checking device of the kind described and illustrated in FIG. 2, with each of the two measuring circuits A and B, checking then taking place simultaneously.

In the case where a single monitoring device is used for both the dose-measuring circuits A and B, the secondary dose-measuring circuit B can be set to a dose level D + d slightly higher than the dose level D preselected on the counters in the main measuring circuit A, or can be arranged to introduce a delay into the dose-measuring function in relation to that performed by the main measuring circuit A. A light or audio signal can be used to indicate that the respective measuring circuits A and B have operated normally during the course of the check.

In the example shown in FIG. 2, the counter system comprises three decades representing for example a counting time of the order of 40 seconds if the frequency of the pulses is 25 Hz. The drive coils $M_1$, $M_2$, $M_3$ can be operated for a time not exceeding $3 \times 9/25 \approx 1$ second.

Figure 3:
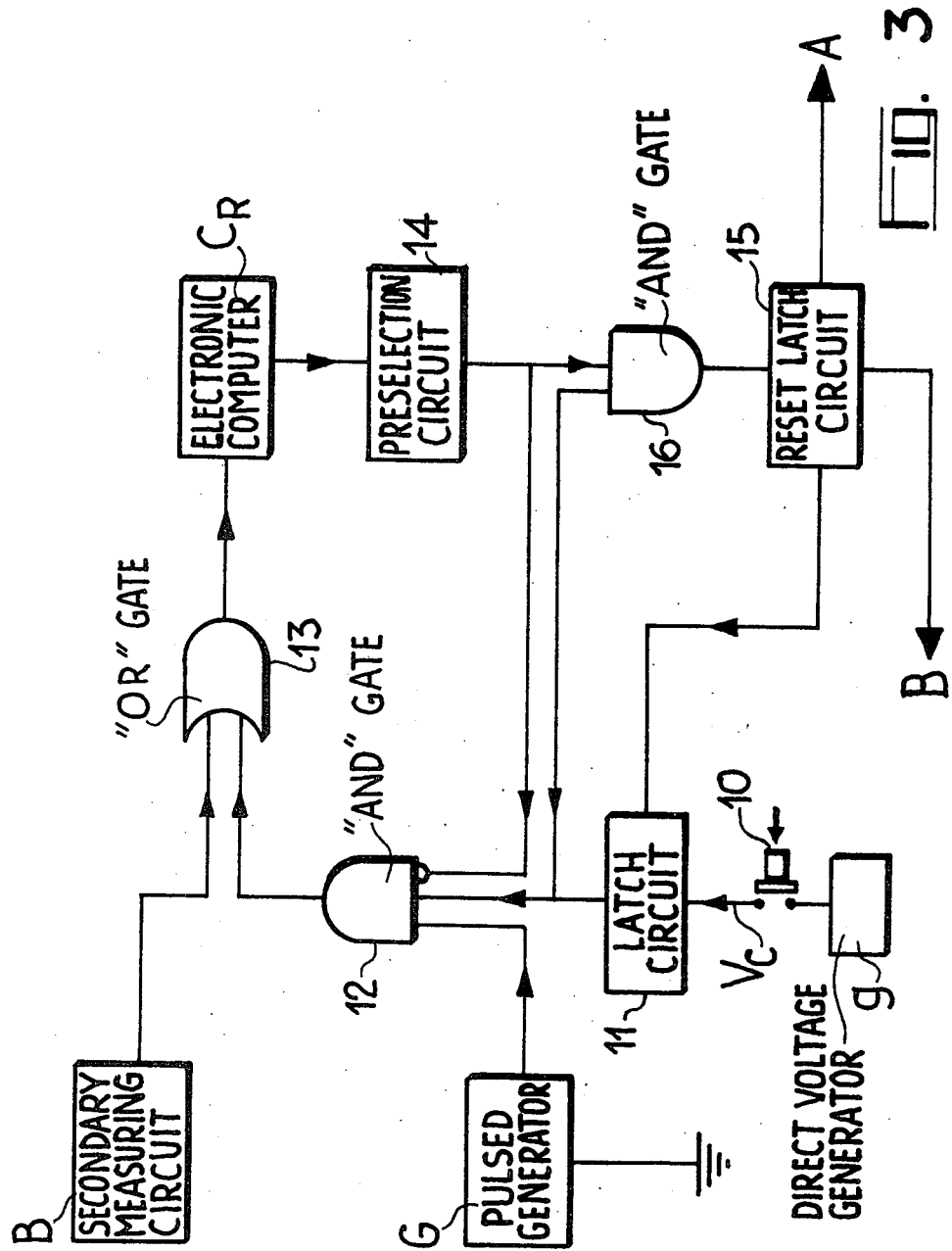

FIG. 3 illustrates another embodiment which is simpler and comprises a type of counters which are faster than the electromechanical counters $C_1$, $C_2$, $C_3$ (for example conventional electronic counters or again a data processor counting system). The electronic counter $C_R$ by means of the AND-gate 12 and the OR-gate 13, as long as direct monitoring voltage $V_c$ is applied to the AND-gate 12 by means of the holding circuit 11 controlled by the contactor 10, and as long as there is no coincidence (AND-gate 16 between the displayed number and the preselected number as determined by the preselect circuit 14. The device 15 for resetting the counter systems of the measuring circuits A and B to zero, is then triggered, this device 15 also controlling the halting of the operating of the circuit 11 which maintains the voltage $V_c$ on the AND-gate 12.

In another embodiment of the checking device in accordance with the invention (shown in FIG. 4), the pulse generator G is associated solely with the second dose-measuring circuit B. This pulse generator G is set into operation by means of a contactor 3 which can be operated when the first or main measuring circuit A has registered, at time $t$, coincidence between the dose level D furnished during a treatment session and the preselected dose level D, this bringing about the halting of the irradiation source. The second measuring circuit B is so designed that it presents a slight delay into the dose level measured (D − ΔD) at time $t$, in relation to the first circuit A, and the pulses furnished by the generator G and supplied to the electromechanical counters $C_1$, $C_2$, $C_3$ will be added to the displayed dose level (D − ΔD), until the second measuring circuit B registers a dose level (D − ΔD + ΔD) corresponding to the preselected value D.

Figure 4:
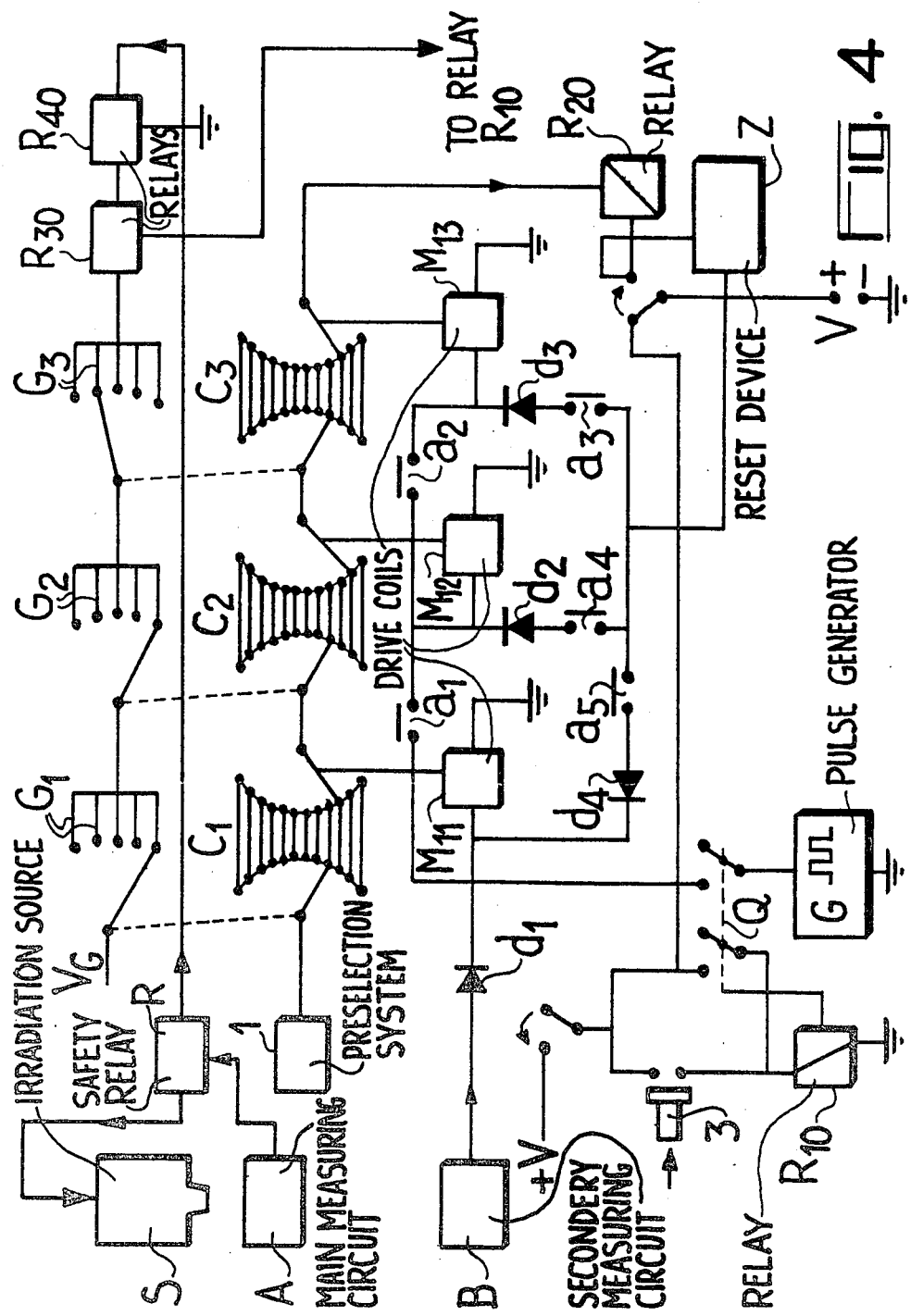

The checking device shown in FIG. 4 comprises:
— a pulse generator G;
— a contactor 3 (a pushbutton for example) operating a relay $R_{10}$ which controls;
— a reversing switch Q making it possible to set the generator G into operation when the measuring circuit A registers a number corresponding to the preselected dose value D corresponding to the halting, by this measuring circuit A, of the irradiation source S;
— drive coils $M_{11}$, $M_{12}$, $M_{13}$;
— isolation diodes $d_1$ to $d_4$;
— contactors $a_1$, $a_2$, $a_3$, $a_4$, $a_5$;
— a relay $R_{20}$ controlling the reset device Z for the counters $C_1$, $C_2$, $C_3$ when the digit indicated by the said counters $C_1$, $C_2$, $C_3$ coincides with the preselected digit corresponding to the preselected dose level D, the number of pulses supplied by the pulse generator G corresponding to the dose level delay ΔD.

In operating, the relay $R_{10}$ is operated manually or, better still, automatically by means of the contactor 3 and is automatically held in the pulled-up state provided that the relay $R_{20}$ has dropped (irradiation source stopped). The pulses from the generator G are then applied to the drive coils $M_{11}$ to $M_{13}$ of the counters $C_1$, $C_2$, $C_3$ causing the latter to advance until coincidence occurs between the display and the preselected figure. At this instant, the relay $R_{20}$ pulls up whilst the relay $R_{10}$ is de-energised, and applied a voltage V to the device Z resetting the counters $C_1$, $C_2$, $C_3$ to zero.

Additional safety means can be associated with the checking device in accordance with the invention as described earlier. Thus, in order to prevent any possibility of the preselected irradiation dose being modified during the course of a radiotherapy treatment or prior to the setting into operation of the checking device as described and illustrated in FIG. 4, a floating contact associated with a system detecting any change in the preselected dose level, can be used to energise the relay $R_{10}$, this protection system comprising slab coils $G_1$, $G_2$, $G_3$ added to each digit of the preselector switch, with non-short circuiting contacts, and two relays $R_{30}$ and $R_{40}$. The relay $R_{30}$ can only actuate the relay $R_{10}$ once the treatment session has ended, that is to say when the relay $R_{40}$ indicates that the first measuring circuit A has operated the system designs for halting the irradiation source S.

What we claim is:
1. A device for checking the operation of an irradiation dose measuring system, said dose measuring system being provided with a first measuring circuit and a second measuring circuit respectively incorporating a first and a second counter system designed to measure the irradiation delivered by an irradiation source S and control the halting of said irradiation source S when the measured dose level corresponds with a preselected dose level D, said checking device comprising a pulse generator G, first means for applying said pulses to said counter system of at least one of said measuring circuits, second means making it possible to halt said pulse generator G, reset said counter system to zero when coincidence is achieved between a preselected number of pulses corresponding to said preselected dose level D and the counted number of pulses, and means for controlling the halting of operation of the irradiation source S.

2. A checking device as claimed in claim 1, wherein said counter systems comprise $n$ electromechanical counters and said first and second means which are associated with each of said measuring circuits comprise:
   a contactbreaker controlling the starting of said pulse generator G;
   $n$ relays associated respectively with $n$ counter drive coils respectively controlling the operation of said $n$ electromechanical counters of each of said measuring circuits;

a relay controlling the halting of the operation of said pulse generator G when the number of counted pulses corresponds with the number of said preselected pulses, and further controlling the resetting to zero of said electromechanical counters.

3. A monitoring device as claimed in claim 2, further comprising a reversing switch to successively apply to said $n$ electromechanical counters of the two measuring circuits, said pulses furnished by said pulse generator G.

4. A monitoring device as claimed in claim 2, further comprising means to simultaneously apply to said $n$ electromechanical counters of the measuring circuits, said pulses furnished by said pulse generator G.

5. A monitoring device as claimed in claim 1, further comprising a system for detecting a change in said preselected dose, said system, associated with said device, comprising:
— slab coils with non-short circuiting contacts, added to each digit of the preselector switch;
— two relays designed to bring about the setting into operation of the monitoring device when halting of the irradiation source S has been verified.

6. A checking device as claimed in claim 1 wherein said pulse generator G is associated with said second measuring circuit, said counter system associated with said second measuring circuit comprising $n$ electromechanical counters, said second measuring circuit presenting a dose measure delay $\Delta D$ with respect to said first measuring circuit, said checking device further comprising further means controlled by said first measuring circuit for setting into operation said pulse generator G when said first measuring circuit registers a number corresponding to said preselected dose D, said pulse generator G delivering to said second measuring circuit pulses corresponding to the delay dose $\Delta D$, means for resetting said electromechanical counters when the measured irradiation dose $(D - \Delta D)$ supplemented by the pulses furnished by said pulse generator G and corresponding to $\Delta D$ is equal to the number of pulses preselected and corresponding to said irradiation dose D.

7. A checking device as claimed in claim 6, comprising in association with said pulse generator G:
a contactor, operating a relay $R_{10}$;
a reversing switch Q for setting the pulse generator G in operation, said reversing switch being controlled by said first measuring circuit after said irradiation dose D corresponding to the preselected value has been delivered and when said irradiation source S has been halted.

* * * * *